United States Patent [19]
Lovejoy et al.

[11] Patent Number: 6,061,584
[45] Date of Patent: May 9, 2000

[54] PULSE OXIMETRY SENSOR

[76] Inventors: David A. Lovejoy, 201 Woodside La., Thiensville, Wis. 53092; George A. Byers, 7786 N. Fairway Pl., Milwaukee, Wis. 53223

[21] Appl. No.: 09/181,739

[22] Filed: Oct. 28, 1998

[51] Int. Cl.[7] .................................................. A61B 5/00
[52] U.S. Cl. ............................................. 600/344; 600/310
[58] Field of Search .................................. 600/310, 322, 600/323, 340, 344, 473, 476

[56] References Cited

U.S. PATENT DOCUMENTS

| | | |
|---|---|---|
| D. 355,032 | 1/1995 | Goldberger et al. . |
| D. 384,643 | 10/1997 | Nierlich et al. . |
| D. 393,830 | 4/1998 | Tobler et al. . |
| 4,305,401 | 12/1981 | Reissmueller et al. . |
| 4,684,245 | 8/1987 | Goldring . |
| 4,690,492 | 9/1987 | Beard . |
| 4,830,014 | 5/1989 | Goodman et al. . |
| 4,838,808 | 6/1989 | Fujiura . |
| 4,938,218 | 7/1990 | Goodman et al. . |
| 4,961,711 | 10/1990 | Fujiura et al. . |
| 4,964,408 | 10/1990 | Hink et al. ................ 600/344 |
| 5,099,842 | 3/1992 | Mannheimer et al. . |
| 5,108,298 | 4/1992 | Simmel . |
| 5,109,849 | 5/1992 | Goodman et al. . |
| 5,125,403 | 6/1992 | Culp . |
| 5,209,230 | 5/1993 | Swedlow et al. . |
| 5,218,962 | 6/1993 | Mannheimer et al. . |
| 5,246,033 | 9/1993 | DeLonzor . |
| 5,249,576 | 10/1993 | Goldberger et al. . |
| 5,337,744 | 8/1994 | Branigan . |
| 5,339,810 | 8/1994 | Ivers . |
| 5,368,025 | 11/1994 | Young et al. . |
| 5,387,122 | 2/1995 | Goldberger et al. . |
| 5,452,717 | 9/1995 | Branigan et al. . |
| 5,469,845 | 11/1995 | DeLonzor . |
| 5,524,617 | 6/1996 | Mannheimer . |
| 5,603,623 | 2/1997 | Nishikawa et al. . |
| 5,638,813 | 6/1997 | Diab . |
| 5,645,440 | 7/1997 | Tobler et al. . |
| 5,660,567 | 8/1997 | Nierlich et al. . |
| 5,678,544 | 10/1997 | DeLonzor et al. . |
| 5,746,206 | 5/1998 | Mannheimer . |

*Primary Examiner*—Eric F. Winakur
*Attorney, Agent, or Firm*—Michael Best & Friedrich; Christian G. Cabou; Phyllis Y. Price

[57] ABSTRACT

A pulse oximetry sensor having an elongate flexible body, an emitter and a detector mounted adjacent the lower surface of the body in a spaced apart relation. First and second attachment members are mounted on the upper surface of the body and are aligned respectively with the emitter and detector. A disposable flexible member has an adhesive on one side and first and second couplers spaced apart a distance equal to that between the first and second attachment members. Each coupler is constructed and arranged to couple to one of the attachment members for coupling the body to the flexible disposable member in cooperation with the adhesive. The member is constructed and arranged to mount the body on a patient with the emitter and detector opposite one another.

9 Claims, 5 Drawing Sheets

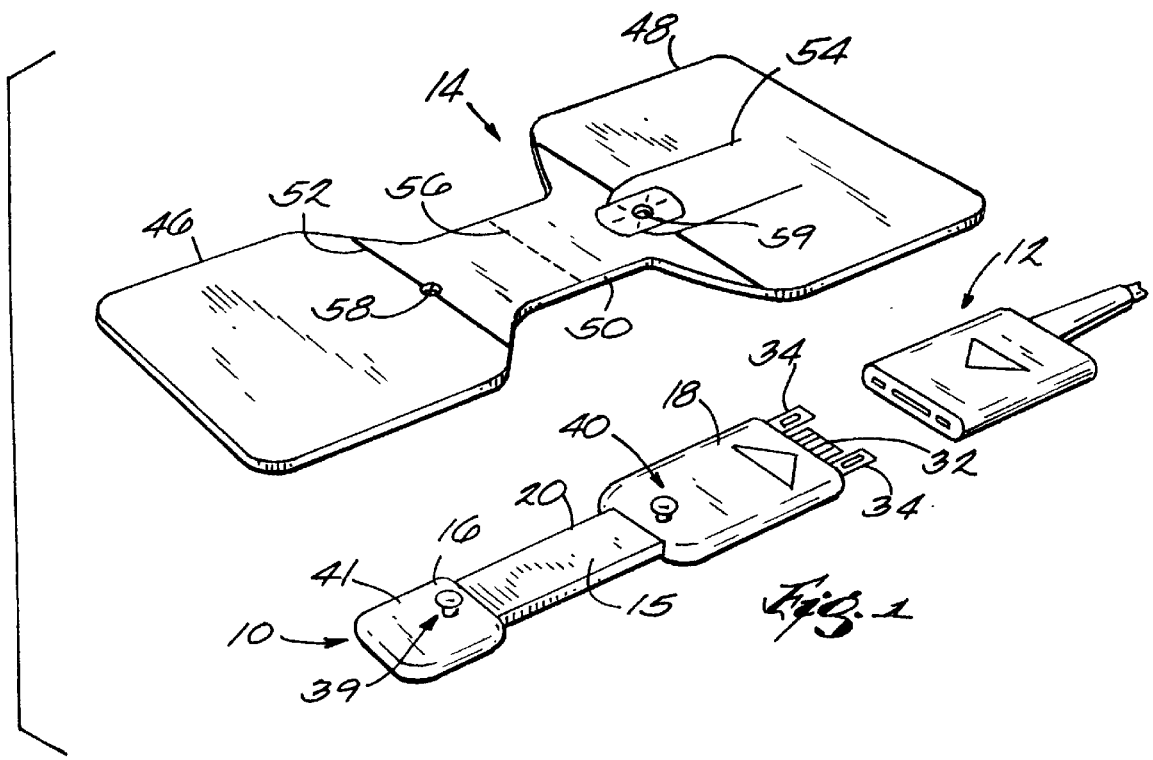
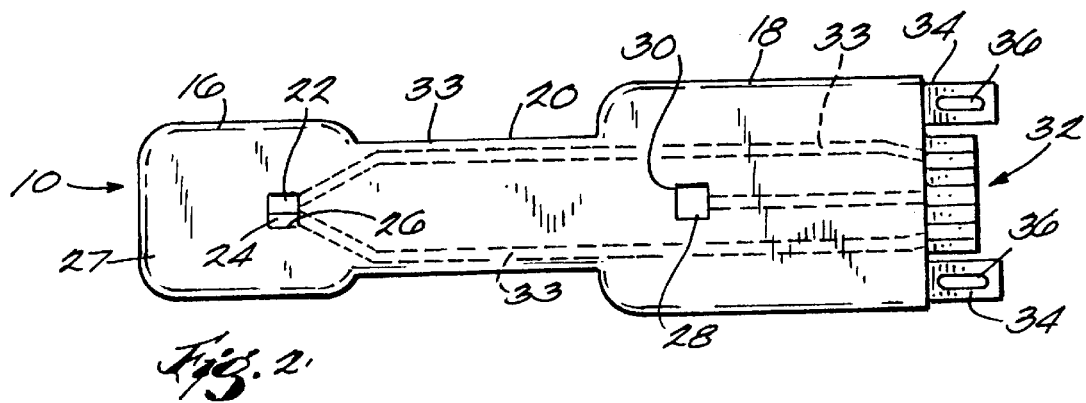
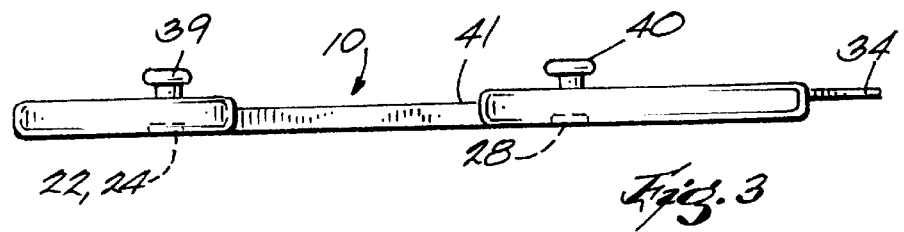

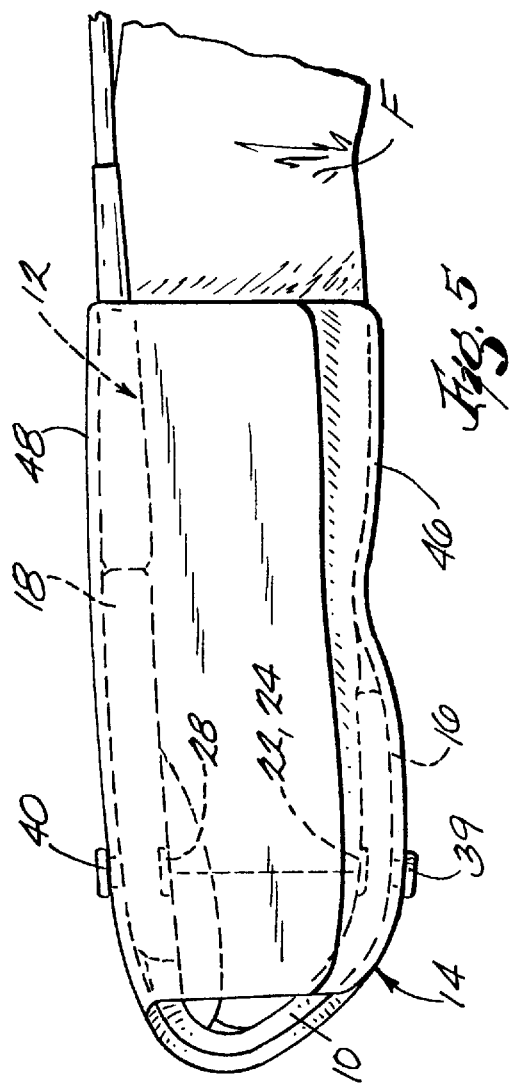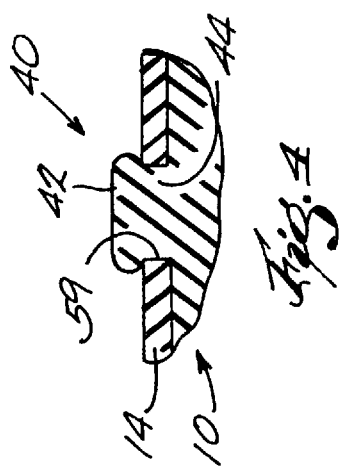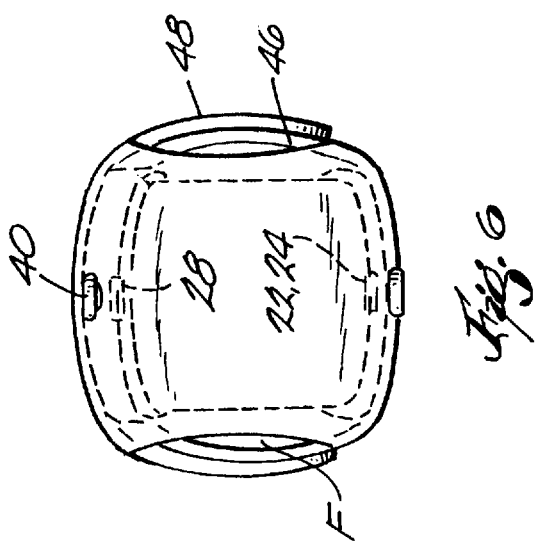

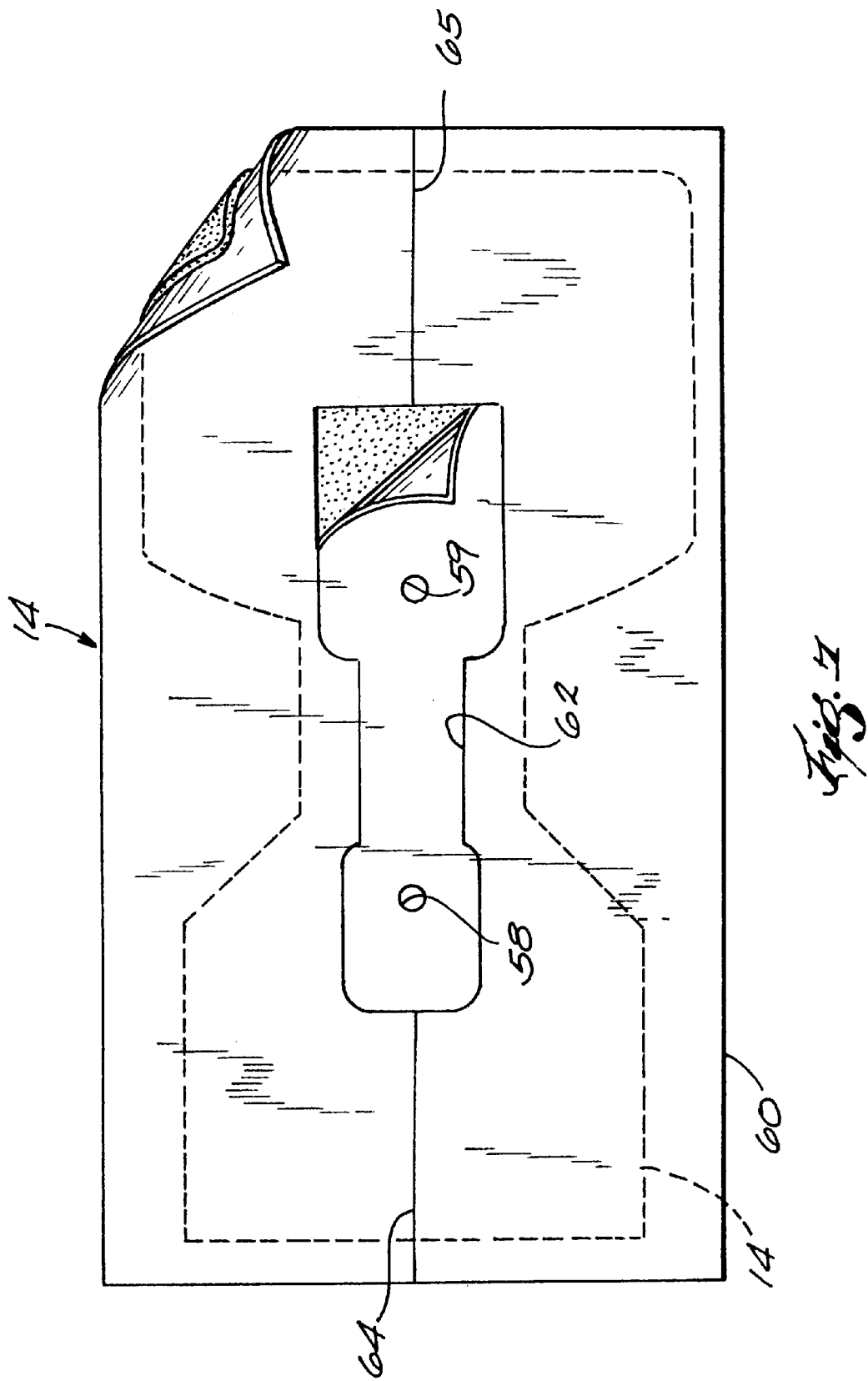

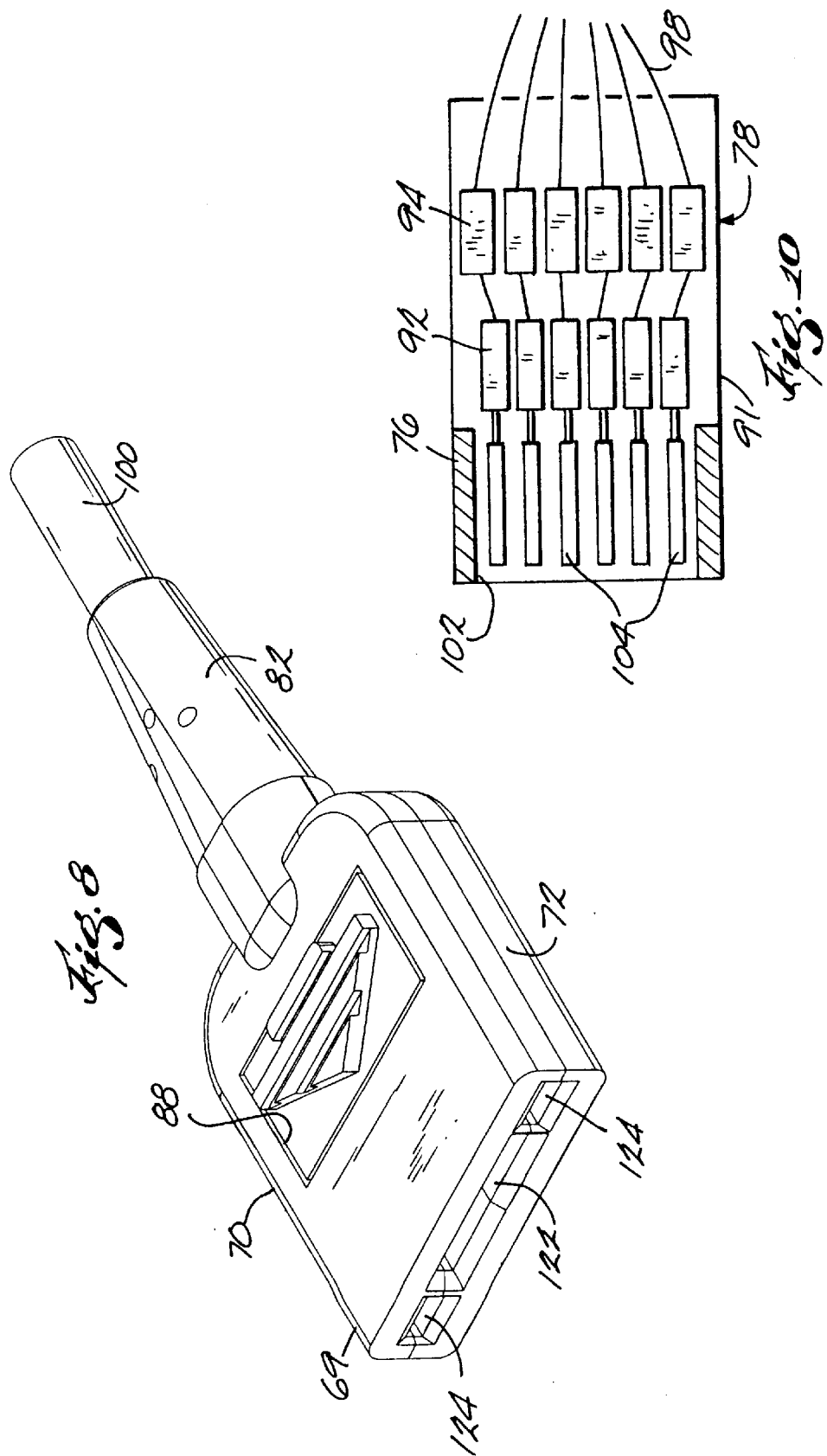

PULSE OXIMETRY SENSOR

BACKGROUND OF THE INVENTION

This invention relates to noninvasive physiologic condition sensors, and more particularly, to noninvasive oximetry sensors.

Noninvasive oximetry commonly takes advantage of the difference in the light absorption coefficient of hemoglobin and oxygenated hemoglobin with respect to light in the red and infrared ranges. This type of oximeter normally includes sensors that are placed against patient tissue which is well profused and includes sources for emitting light at one or more wavelengths into the tissue and a light detector for detecting the amount of light which passes through the tissue. The amount of light absorbed at each wavelength is used to calculate oxygen saturation in the patient's blood in accordance with Lambert-Beer's law. Such sensors are normally placed on the fingertip, earlobe, nasal septum or forehead of the patient and preferably include means for retaining the sensor in position for the extended periods during which such measurements are made.

One type of prior art pulse oximetry sensor is disclosed in U.S. Pat. No. 4,830,014 and includes an emitter and detector mounted on an adhesive pad for being secured to the patient. Leads are connected to the emitter and detector for connection to a monitor. For sanitary reasons, such sensors are normally disposable.

A similar type of sensor is shown in U.S. Pat. No. 5,209,230 wherein the emitter is mounted on a disposable adhesive pad and the detector is mounted in a housing which is detachable from the pad to permit reuse. The per use expense of such prior art sensors is relatively high because either one more of the components, such as, the emitter, the detector, the connector, or the cable are commonly discarded after a single use.

To insure accurate results, it is desirable that the emitter and detector be positioned in an opposed relation on the opposite side of the patient's finger or earlobe. For this purpose, prior art oximetry sensors commonly include alignment markings printed on the outer surface of the adhesive pad. However, these alignment marks may not always be clearly visible on both sides of the finger or earlobe simultaneously and in more than one perspective which makes alignment more difficult.

SUMMARY OF THE INVENTION

It is an object of the invention to provide a new and improved pulse oximetry sensor.

A further object of the invention is to provide a pulse oximetry sensor in which the emitter and detector are reusable.

Another object of the invention is to provide a new and improved means for attaching a multi-use sensor to an adhesive appliance.

It is a further object of the invention to provide a new and improved means for registration of a sensor to an adhesive appliance.

Another object of the invention is to provide a pulse oximetry sensor which includes alignment markers visible from various perspectives.

Yet another object of the invention is to provide a new and improved means for attaching a sensor to an adhesive appliance.

It is a further object of the invention is to provide a new and improved connector for pulse oximetry sensors.

It is a still further object of the invention to provide a new and improved means for insuring a proper connection between a sensor and a connecting cable.

These and other objects and advantages of the present invention will become more apparent from the detailed description thereof taken with the accompanying drawings.

In general terms, the invention comprises a pulse oximetry sensor including an elongate flexible body, an emitter and a detector mounted adjacent the lower surface of the body in a spaced apart relation. First and second attachment members are mounted on the upper surface of the body and are aligned respectively with the emitter and detector. A disposable flexible member has an adhesive on one side and first and second couplers spaced apart a distance equal to that between the first and second attachment members and each coupler is constructed and arranged to couple to one of the attachment members for coupling the body to the flexible disposable member in cooperation with the adhesive. The member is constructed and arranged to mount the body on a patient's tissue with the emitter and detector on the opposite sides thereof, with each attachment member and coupler defining a coupled pair extending above the surface of the flexible member and aligned respectively with the emitter and detector. Each flexible pair is visible when the flexible member and the body are mounted on the patient's tissue to permit alignment of the emitter and detector on the opposite sides thereof.

BRIEF DESCRIPTION OF THE DRAWINGS

FIG. 1 is an exploded perspective view of the sensor according to the invention;

FIG. 2 is a top plan view of a portion of the sensor illustrated in FIG. 1;

FIG. 3 is a side view of the sensor portion shown in FIG. 2;

FIG. 4 is an enlarged sectional view of a portion of the sensor shown in FIGS. 2 and 3;

FIG. 5 is a side view of the sensor mounted on the appendage of a patient;

FIG. 6 is a front view of the sensor mounted on the appendage of a patient;

FIG. 7 is a bottom view of the flexible pad portion of the sensor shown in FIG. 1;

FIG. 8 is a perspective view of the connector portion of the sensor shown in FIG. 1;

FIG. 10 is a view taken along lines 10—10 of FIG. 9.

DETAILED DESCRIPTION OF THE PREFERRED EMBODIMENT

Figure 9:
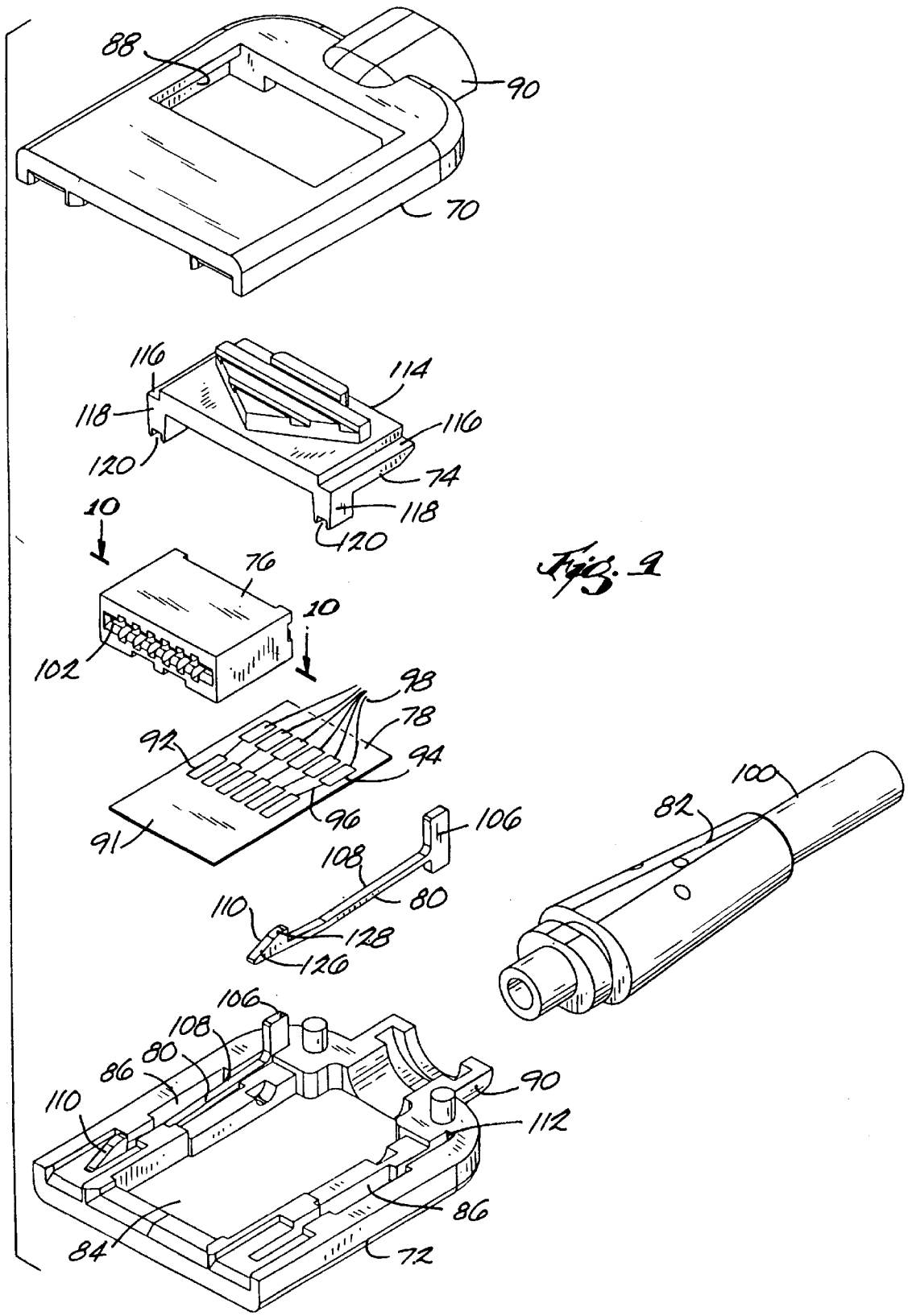
FIG. 9 is an exploded perspective view of the connector shown in FIG. 8.

The oximetry sensor according to the preferred embodiment of the invention is shown in FIGS. 1–6 to include an emitter and detector module 10, a connector 12 and an adhesive pad 14. The connector 12 connects the module 10 to a monitor (not shown) and the adhesive pad 14 secures the module 10 and connector 12 to the patient's tissue, which in FIGS. 5 and 6 is shown to be a finger.

The module 10 includes a body 15 formed of a suitable flexible, impervious, electrically insulating material, such as, rubber, plastic or neoprene. As seen in FIGS. 1–3, the body 15 is relatively flat and includes a detector portion 16, an emitter portion 18 and a reduced width connecting portion 20. The configuration of the module 10 is determined by the patient body area upon which it is to be mounted. The embodiments of FIGS. 1–6 is configured for being mounted on the patient's finger. If the module is to be mounted on an ear, nose, or for neonatal use, the configuration would be appropriate for such use.

Mounted in the emitter portion 18 are a pair of emitters, which in the illustrated embodiment are light emitting diodes 22 and 24, one of which projects light in the red range and the other in the infra red range. Emitters 22 and 24 are each exposed through a window 26 in the lower surface 27 of the body 15. Light detector 28 is disposed in the detector portion 18 and is exposed through a second window 30 in the lower surface of body 15. The detector 28 may also be recessed from the surface of body 15 so that it is shielded from ambient light.

The emitters 22 and 24 and the detector 28 are preferably mounted on a flexible, plastic substrate 32 encapsulated in the body 15. Also disposed on the substrate 32 are electrical conductors 33, one pair of which are respectively connected to the emitters 22 and 24 and the detector 28. The end of the substrate 32 and the conductors 33 extend from one end of the detector portion 18 for being coupled to the connector 12 as will be described more fully below. A pair of catches 34 also extend from the end of the detector portion 18 and on the opposite sides of the substrate 32 but in a different longitudinal plane. The catches 34 may be formed of any suitable material, such as, a plastic or metallic material and each has a hole 36 in its free end. In addition, a pair of mushroom-shaped mounting members 39 and 40 are integrally formed on the upper surface 41 of the body 15. As seen in FIG. 4, each of the mounting members 39 and 40 includes a head portion 42 and a reduced diameter stem portion 44. With reference to FIGS. 3, 5 and 6 it can be seen that the mounting member 39 is aligned with the emitters 22, 24 and the mounting member 40 is aligned with the detector 28.

The flexible adhesive pad 14 is generally butterfly shaped and includes a pair of wing sections 46 and 48 and an interconnecting center section 50. Alignment marks 52 and 54 are printed on the upper surface of the wings 46 and 48 and an additional alignment mark 56 is provided on the center portion 50. In addition, wings 46 and 48 have holes 58 and 59, respectively, which are spaced apart a distance equal to that between the mounting members 39 and 40. As seen in FIG. 4, the diameter of hole 58 is about equal to or slightly smaller than the diameter of the stem portion 44 of the mounting members 39 and 40.

FIG. 7 shows the adhesive pad 14 mounted on a backing sheet 60. To facilitate mounting, the backing sheet 60 has a first cut line 62 which conforms generally to the shape of the module 10 and encompasses the holes 58 and 59. In addition, cut lines 64 and 65 extend from the cut line 62 to the opposite edges of the sheet 60.

The connector 12 is shown in FIGS. 8–10 to include a housing 69 comprising upper and lower housing portions 70 and 72, an operator on push button 74, a terminal block 76, a contact pad 78, a pair of latches 80 and a cable termination cone 82.

The lower housing portion 72 includes a generally rectangular central cavity 84 for receiving the terminal block 76 and the contact pad 78. In addition, there are a pair of slots 86 formed along the sides of the lower housing portion 72 for receiving the latches 80. The slots 86 are parallel to each other and spaced apart a distance equal to that between the catches 34. The upper housing portion 80 has a window 88 for receiving the push button 74 and the upper and lower housing portions 70 and 72 have opposed cable guides 90 for receiving the cable termination cone 82.

The contact pad 78 includes a non-conductive substrate 91 and front and rear rows of contacts 92 and 94, respectively, and corresponding in number to the number of conductors 33 on the substrate 32. The corresponding contacts 92 and 94 in each row are interconnected by conductors 96 and each of the contacts 94 in the rear row are connected to a conductor 98 which extends into the cable termination cone 82 and forms a cable 100.

FIG. 10 illustrates how the terminal block 76 is mounted on the contact pad 78. In particular, the terminal block 70 comprises a molded plastic member of a suitable non-conductive material and includes a central, generally rectangular cavity 102. On the lower surface of the cavity 102, there are conductive contact strips 104 corresponding in number to the conductors 33 on the substrate 32. At the rear, the contact strips 104 extend downwardly and each is connected to a corresponding contact in the front row of contacts 92.

Each latch 80 includes a generally rectangular rear anchor member 106, an elongated central flexible portion 108 and a front hook portion 110. The anchor members 106 are received in generally rectangular recesses 112 in the opposite sides of the lower housing portion 72 at the rear of the slots 80. There are also corresponding rectangular recesses (not shown) in the upper housing portion 70. These cavities retain the latches 80 against longitudinal or transverse movement. The central flexible portions 108 and the hooked portions 110 of each latch 80 are received in the slots 86 and are free to flex downwardly.

The push button 74 includes a central portion 114 which is complimentary to the window 88 in the upper housing portion 70 and a pair of laterally extending shoulders 116 which extend beneath the lower surface of housing portion to retain the push button within housing 69. In addition, there are a pair of downwardly extending legs 118 spaced apart a distance equal to that of the latch members 80 and each leg has a downwardly facing groove 120 for engaging one of the flexible portions 108 of latches 80.

The housing portions 70 and 72 may be joined in any suitable manner as seen in FIG. 8. When so connected, they define a generally rectangular front opening 122 which communicates with the recess 102 in the terminal block 78 and a pair of laterally spaced openings 124 which communicate with the slots 80.

In order to couple the module 10 to the connector 12, the substrate 32 is inserted into the opening 122 and the catches 34 are simultaneously inserted into the openings 124. Because the catches 34 and the substrate 32 lie in different planes and similarly because the center lines of the openings 124 lie in a different plane than the center line of the opening 122, substrate 32 and the catches 34 can only enter the openings 122 and 124 respectively if the module 10 and the connector are properly oriented. When the catches 34 enter the openings 124, their forward ends engage the inclined surfaces 126 on the forward end of the hook portions 110 to force the hooked portions downwardly thereby permitting the catches 34 to proceed inwardly. When the flat upper surface 128 of each of the hook portions 110 is in alignment with the openings 36 in the catch members 34, the hook portions 110 flex upwardly moving the hook portions 110 into the openings 36 and thereby latching the two together. When it is desired to uncouple the module 10 from the connector 12, the push button 74 is depressed whereby its downwardly depending legs 118 force the latch members 80 to flex downwardly moving the hook portions 110 out of the holes 36 so that the module 10 may be moved outwardly.

When the module is coupled to the connector 12, the conductors 33 on the substrate 32 engage the contact strips 104 on the terminal block 78 thereby completing the electrical connection between the emitters 22 and 24 and the detector 28 with the cable 100. It will be appreciated that at the opposite end of the cable 100 there is a connector for coupling the cable to a monitor (not shown).

After the module 10 has been coupled to the connector 12, the portion of the backing paper 60 surrounding by the cutline 62 is removed and the adhesive pad is applied to the module 10 with the mounting members 39 and 40 extending through the holes 58 and 59, respectfully. The adhesive material on the pad 14 and the head portions 42 retain the module 10 and pad 14 in engagement. After the module 10 has been mounted on the pad 14, the module and pad are then placed on the finger of the patient. In so doing, the technician aligns the mounting members 39 and 40 in both the side and front views as shown in FIGS. 5 and 6. This ensures that the emitters 22 and 24 are properly aligned with the detector 28. The wing portions 46 and 48 of the pad 14 is then applied to the patient's finger to hold the module in position during the measurements which may last for a considerable After the pulse oximetry measurements have been completed, the pad 14 is removed from the patient's finger. Thereafter, module 10 is removed from the pad 14 and the pad discarded. However, because the module 10 is imperious, it may be removed from the connector 12 and sterilized for reuse. In this manner, only the relatively inexpensive adhesive pad 14 need be discarded while the module with its relatively more expensive electrical components can be reused.

While only a single embodiment of the invention has been illustrated and described, it is not intended to be limited thereby but only by the scope of the appended claims.

We claim:

1. A physiologic condition sensor comprising
   an elongate flexible body having upper and lower surfaces, an emitter and a detector mounted on the body in a spaced apart relation adjacent to the lower surface thereof,
   first and second attachment members mounted on the upper surface of the body and being aligned respectively with the emitter and the detector,
   a disposable flexible member having an adhesive on one side thereof, and first and second couplers spaced apart a distance equal to that between the first and second attachment members and each being constructed and arranged to couple to one of the attachment members for coupling the body to the flexible member in cooperation with said adhesive, the flexible member being constructed and arranged to mount the body on a patient's tissue with the emitter and detector on the opposite sides thereof,
   each attachment member and coupler defining a coupled pair aligned respectively with the emitter and detector, each coupled pair extending above the surface of the flexible member and being visible when the flexible member and the body are mounted on the patient's tissue to permit alignment of the emitter and the detector on the opposite sides thereof.

2. The sensor set forth in claim 1 and including a support extending from one end of the body, at least one conductor connected to each of the emitter and detector and extending through the flexible body and onto the support in a spaced apart relation, and a connector having means for receiving the support and contacts for electrically engaging the conductors.

3. The sensor set forth in claim 2 wherein the flexible member also engages the connector when coupled to the body to secure the connector to the body.

4. The sensor set forth in claim 1 wherein the first and second couplers each include a hole in the flexible member sized to receive, respectively, said first and second attachment members therethrough.

5. The sensor set forth in claim 4 wherein said attachment members each includes a stem portion extending from said body and an enlarged head portion, said holes being smaller than the head portions and sized to be received over said stem portions.

6. A physiologic condition sensor comprising:
   an elongate flexible body having upper and lower surfaces, an emitter and a detector encapsulated in the body in a spaced apart relation and adjacent to the lower surface thereof, a substrate extending from one end of the flexible body, at least one conductor connected to each of the emitter and the detector and extending through the flexible body and onto the substrate in a spaced apart relation, a connector including a housing having an opening for receiving the substrate, contacts disposed in the housing for electrically engaging the conductors, at least one resilient latch member disposed in the housing, a catch member mounted on the body and engageable with the latch member when the substrate is received in the opening for being engaged by the latch member to latch the body to the connector, and an operator engageable with the latch member and operative when manually engaged to flex the latch member out of engagement with the catch member so that the body can be separated from the connector.

7. The sensor set forth in claim 6 and including first and second attachment members mounted on the upper surface of the body and being aligned, respectively, with the emitter and the detector, a disposable flexible member having an adhesive on one side thereof, and first and second couplers spaced apart a distance equal to that between the first and second attachment members and each being constructed and arranged to couple to one of the attachment members for coupling the body to the flexible member in cooperation with said adhesive, the flexible member being constructed and arranged to mount the body on a patient's tissue with the emitter and the detector on the opposite sides thereof, each attachment member and coupler defining a coupled pair aligned respectively with the emitter and the detector, each coupled pair extending above the surface of the flexible member and being visible when the flexible member and the body are mounted on the patient's tissue to permit alignment of the emitter and the detector on the opposite sides thereof.

8. The sensor set forth in claim 7 wherein the flexible member also engages the connector when coupled to the body to secure the connector to the body.

9. A physiologic condition sensor comprising:
   a flexible body having upper and lower surfaces, and an emitter and a detector mounted on the body in a spaced apart relation adjacent to the lower surface thereof;

first and second attachment members mounted on the upper surface of the body and being aligned respectively with the emitter and the detector;

a flexible member having an adhesive on one side thereof and first and second couplers spaced apart a distance equal to that between the first and second attachment members, each coupler being constructed and arranged to couple to one of the attachment members so as to couple the body to the flexible member, the flexible member being constructed and arranged to mount the body on a patient's tissue with the emitter and detector on the opposite sides thereof;

each attachment member and coupler defining a coupled pair aligned respectively with the emitter and detector, each coupled pair extending above the surface of the flexible member and being visible when the flexible member and the body are mounted on the patient's tissue to permit alignment of the emitter and the detector on the opposite sides thereof.

\* \* \* \* \*